United States Patent [19]
Tanhehco

[11] Patent Number: 5,915,461
[45] Date of Patent: Jun. 29, 1999

[54] HEAT PACK AND TRIGGER APPARATUS

[75] Inventor: Benito Li Tanhehco, Powell, Tenn.

[73] Assignee: DeRoyal Industries, Inc., Powell, Tenn.

[21] Appl. No.: 09/052,393

[22] Filed: Mar. 31, 1998

[51] Int. Cl.$^6$ ....................................................... F28F 7/00
[52] U.S. Cl. .............................. 165/46; 165/10; 126/204;
126/263.01; 126/263.03; 126/263.07; 126/263.08;
126/263.09
[58] Field of Search ................... 165/10, 46; 126/263.01,
126/263.02, 263.03, 263.06, 263.07, 263.04,
263.08, 263.05, 263.09, 263.1, 204

[56] References Cited

U.S. PATENT DOCUMENTS

| | | | |
|---|---|---|---|
| 1,384,747 | 7/1921 | Eckelmann et al. | 126/263.03 |
| 2,157,169 | 5/1939 | Foster | 126/263.01 |
| 3,951,127 | 4/1976 | Watson et al. | 126/263.03 X |
| 4,106,478 | 8/1978 | Higashijima | 126/263.02 X |
| 4,361,491 | 11/1982 | Truelock | 126/263.03 X |
| 4,503,838 | 3/1985 | Arrhenius | 165/10 X |
| 4,888,188 | 12/1989 | Castner, Sr. et al. | 126/263.04 X |
| 5,143,048 | 9/1992 | Cheney, III | 126/263.04 |
| 5,275,156 | 1/1994 | Milligan et al. | 126/263.04 X |
| 5,305,733 | 4/1994 | Walters | 126/204 X |
| 5,534,020 | 7/1996 | Cheney, III et al. | 126/204 X |
| 5,662,096 | 9/1997 | Walters | 126/263.03 |

FOREIGN PATENT DOCUMENTS

| | | | |
|---|---|---|---|
| 639489 | 4/1962 | Canada | 126/263.09 |
| 356061549 | 5/1981 | Japan | 126/263.08 |
| 360101449 | 6/1985 | Japan | 126/263.08 |
| 362000765 | 1/1987 | Japan | 126/263.09 |
| 088008110 | 10/1988 | WIPO | 126/263.1 |

*Primary Examiner*—Ira S. Lazarus
*Assistant Examiner*—Christopher Atkinson
*Attorney, Agent, or Firm*—Pitts & Brittian

[57] ABSTRACT

A heat pack including apparatus for triggering the crystallization of a supercooled salt solution in the heat pack, wherein the supercooled salt solution is sealed within a flexible package. The apparatus comprises a solid trigger device, and a packet having at least one wall. The solid trigger device and crystals of the salt of the supercooled salt solution are located in the packet and the packet is sealed to at least one of the walls of the flexible package. Thus, the packet is in intimate positional relationship with the supercooled salt solution. The solid trigger device is forced to pierce the packet and deliver salt crystals from the packet to the supercooled salt solution thereby triggering crystallization of the supercooled salt solution and producing heat.

4 Claims, 2 Drawing Sheets

HEAT PACK AND TRIGGER APPARATUS

FIELD OF INVENTION

The present invention relates generally to apparatus for initiating the crystallization of a supercooled material such as those used for phase-change thermal energy storage. Such crystallization causes the super-cooled material to change from its high-temperature phase to its low-temperature phase very rapidly and, in doing so, surrender its latent heat of transition.

BACKGROUND OF THE INVENTION

The principles of thermal energy storage in phase-change materials are well known. As the materials are heated from an initial phase, such as the solid phase, to a second phase, such as the liquid phase, energy is absorbed. In the temperature range at which the material changes from one phase to another, more energy is required to raise the temperature an additional increment than to raise the temperature by the same increment when the material is not changing phase. This additional energy required at the phase change of the material is called the latent heat of transition.

The heat required for the phase change from liquid to gas is called the latent heat of vaporization. The heat required for the phase change from solid to liquid (and give up in the reverse phase change from liquid to solid) is known as the latent heat of fusion. When a material cools, the energy absorbed at the phase-change point is normally given up. Some materials will cool well below the normal phase change temperature, but still retain the latent heat of transition and remain in the higher temperature phase or state. For example, some materials under some circumstances may be cooled below the temperature at which they normally change from liquid to solid yet remain in the liquid state, thus still retain the latent heat of fusion. A material in this condition is said to be undercooled or supercooled. It is possible to create conditions in an undercooled material that will cause it to change very rapidly from the high-temperature phase to the low-temperature phase, thus giving up the energy stored at the latent heat of transition or fusion rapidly. The energy so released may be put to practical use in many ways.

One example of such a use is as a heel warmer with new borns. Most hospitals require that blood samples be taken from new born infants during the first days after birth. Since one of the biggest body masses of a new born is the heel, blood for tests is generally drawn from the heel area. The problem with the heel as a source of blood is that a new born's blood circulation is poor. If blood circulation in the heel area is not increased before testing, drawing blood for testing may have an adverse affect on the infant and cause complications.

It is well known that heat causes blood flow to increase at the site where the heat is applied. Heat applied to the new born's heel area before blood is drawn for testing will increase blood flow into the heel area and prevent complications from the test. Heat packs have long been used in various forms in the medical and sports fields, and they are particularly useful for warming the heels of new born infants before blood is drawn for various tests.

The art relating to the preparation and use of supercooled salt solutions for heat packs is extensive and there are a large number of different solutions that are effective. Such solutions include, but are not limited to, sodium acetate, sodium thiosulfate, trimethylol ethane hydrates, and the like. In general, the salt and a solvent (most often the solvent is water) are mixed together and then heated to a temperature where all of the salt is dissolved in the solvent. The solution is then allowed to cool slowly to around room temperature.

The triggering of the supercooled solution to activate the crystallization has been accomplished in a number of ways. Often a simple shock to the supercooled salt solution will cause crystallization. However, this type of situation can result in the premature crystallization and release of heat. Thus, the salt crystals in the heat pack will need to be redissolved prior to use.

A variety of devices have been tried for triggering crystallization. For example, U.S. Pat. No. 5,275,156 to Milligan, et al., discloses a trigger device that floats free in the supercooled salt solution which is activated by applying pressure to the device; U.S. Pat. Nos. 4,460,546, 4,899,727 and 4,580,547 to Kapralis, et al., disclose the use of another set of trigger devices which float free in the supercooled salt solution (generally, Kapralis, et al., disclose concave discs which are caused to "snap" in order to activate the heat pack); U.S. Pat. No. 5,056,589 to Hettel, et al., discloses the use of metallic spring mechanism for crystallizing a supercooled salt solution; and U.S. Pat. No. 5,143,048 to Cheney, III, describes a trigger device which comprises a disc or ampule containing crystals of the salt used to form the supercooled salt solution (the disc or ampule is broken and the crystals are exposed to the supercooled salt solution).

There are numerous other devices for activating supercooled salt solutions and each of them has its own advantages. However, the devices of the prior art, in general, have the disadvantage of requiring the user to locate the triggering device prior to activation. The triggering devices usually are floating free in the supercooled salt solution. They must be located in the solution, restrained to a particular position in the heat pack and then activated by some manipulation of the user. It is desirable to have a triggering device which can be used without the necessity of a person having to locate and restrain the triggering device in the supercooled salt solution.

Therefore, it is an object of the present invention to provide a triggering device for a supercooled salt solution type heat pack which provides a trigger that is located in a fixed location relative to, but physically from, the supercooled salt solution.

It is also an object of the present invention to provide such a triggering device which is easy and intuitive to use.

Consideration of the specification, including the several figures to follow, will enable one skilled in the art to determine additional objects and advantages of the invention.

SUMMARY OF THE INVENTION

Having regard to the above and other objects and advantages, the present invention generally provides apparatus for triggering the crystallization of a supercooled salt solution in the pack package, wherein the supercooled salt solution is sealed within a flexible package having at least two walls. The apparatus, in a preferred embodiment, comprises a solid, generally planar trigger device, and a flexible packet having at least one wall and containing a chemical moiety capable of initiating crystallization of the supercooled salt solution. The solid trigger device is located in the packet and the packet is sealed to at least one of the walls of the flexible package. Thus, the packet is disposed immediately contiguous to the supercooled salt solution but is physically separated from the salt solution by at least one wall of the flexible heat pack package. The solid trigger device includes a first end which defines means for piercing a wall of the packet and a second end defining a blunt surface for engagement by a force—generating instrumentality.

Application of a force to the blunt second end of the trigger causes the first end thereof to pierce the flexible packet and at least partially enter the heat pack and, in the preferred embodiment, deliver to the salt solution in the heat pack, the chemical moiety which initiates crystallization of the supercooled salt solution and resultant production of heat.

The supercooled salt solution comprises a mixture of the solid crystals of a salt (such as sodium acetate, sodium thiosulfate, trimethylol ethane hydrates, and the like) with a solvent (such as water) and is contained in the heat pack package. In a preferred embodiment of the present invention, the packet containing the trigger further comprises solid crystals of the same salt that is dissolved in the supercooled salt solution.

DETAILED DESCRIPTION OF INVENTION

Figure 1:
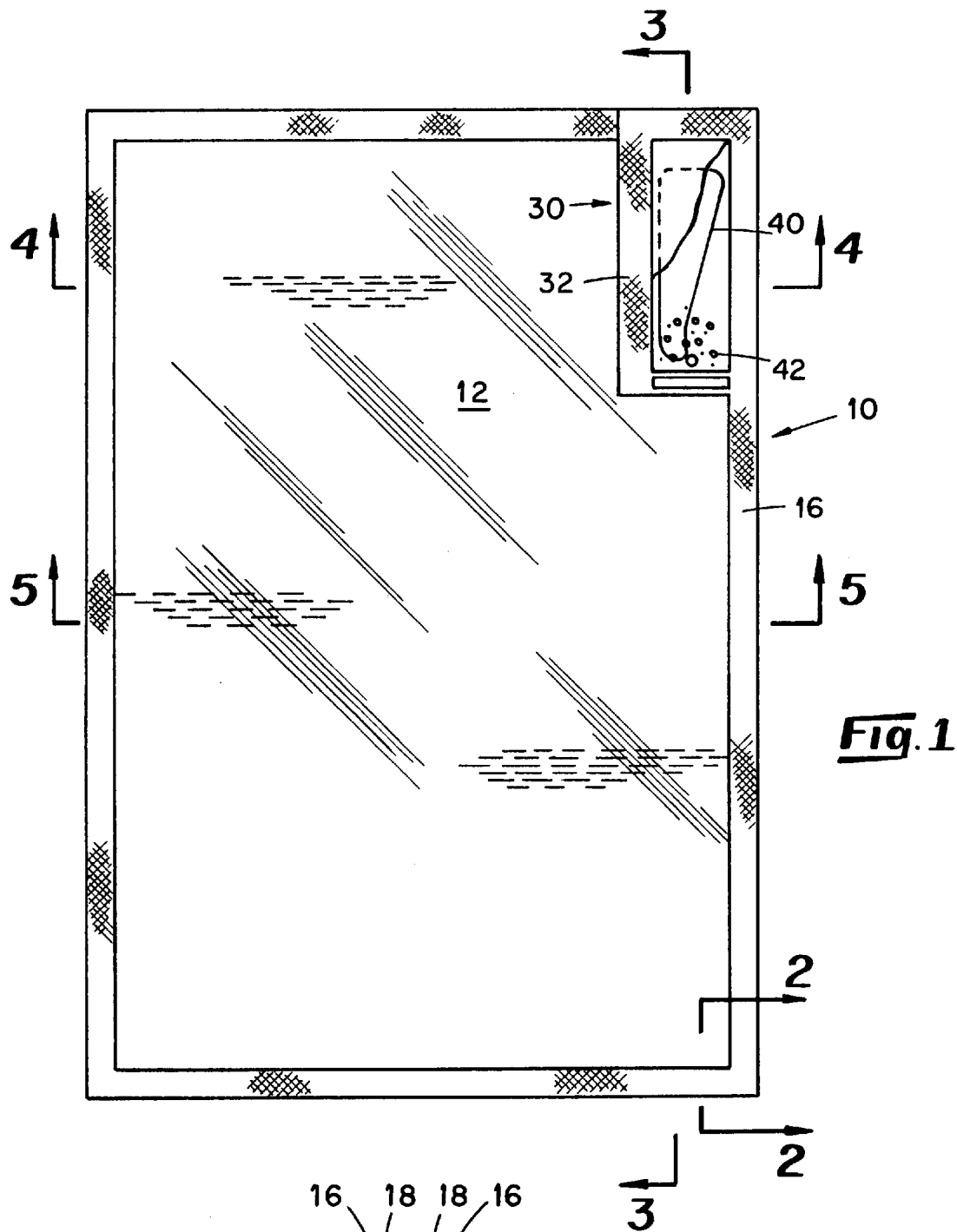
FIG. 1 is a front elevational view of one embodiment of a heat pack embodying various of the features of the present invention.
Figure 2:
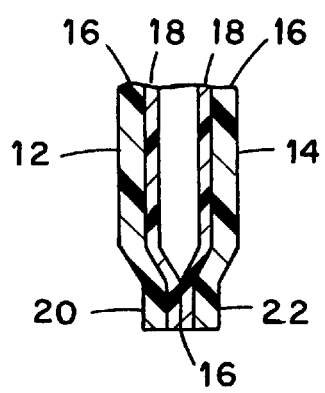
FIG. 2 is a sectional view depicting one construction of the walls of the heat pack depicted in FIG. 1 and taken along the line 2—2 of FIG. 1.
Figure 3:
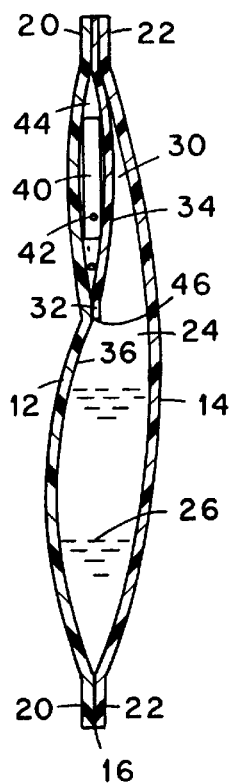
FIG. 3 is a sectional view of the apparatus depicted in FIG. 1 and taken along the line 3—3 thereof.
Figure 4:
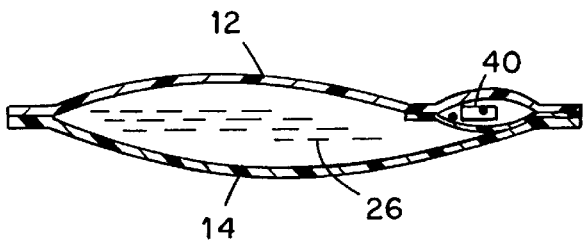
FIG. 4 is a sectional view of the apparatus depicted in FIG. 1 and taken along the line 4—4 thereof.
Figure 5:
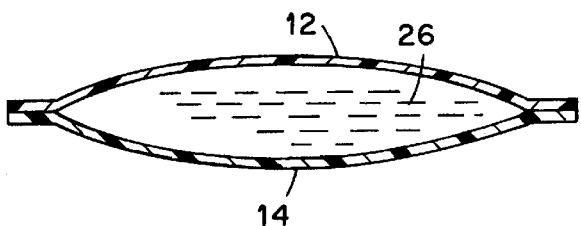
FIG. 5 is a sectional view of the apparatus depicted in FIG. 1 and taken along the line 5—5 thereof.

With reference to FIGS. 1–4, the depicted embodiment of the present invention includes a heat pack 10 formed in the nature of a pouch and having first and second layers of a flexible, preferably transparent, plastic material. These layers may be formed of the same plastic, but if desired, a different plastic may be employed for each of the layers and/or each layer may comprise a laminate of different plastic materials. In a preferred embodiment, each of the layers 12 and 14 comprises a laminate made up of an outer layer of nylon 16 (or polyvinylchloride) which is pin-hole free, and an inner layer of high density polyethylene 18. Whereas the inner layer 18 is depicted in the Figures as being coextensive with the outer layer 16, it is suitable, if desired, to provide a frame of the inner layer 18 about the perimeter of the heat pack inasmuch as the primary function of this inner layer is to form a perimetral seal between the first and second layers 12 and 14. In forming the heat pack, the layers 12 and 14 are overlaid in register with one another, with the polyethylene layers of each of the laminates disposed in facing relationship. Thereafter, the perimetral edges 20 and 22, respectively, of the layers 12 and 14 are bonded to one another, preferably by heat sealing, to define a closed pouch 24 for containing a supercooled salt solution 26.

In the embodiment of the present invention depicted in the Figures, there is provided a packet 30, preferably disposed in one inside corner of the heat pack 10. This packet preferably is formed by heat sealing the perimeter 32 of a patch 34 of plastic material to the inner surface 36 of the first layer 12 of the heat pack 10 thereby defining a sealed container for a trigger 40 and crystals 42 of the salt of the supercooled salt solution. In one embodiment of the fabrication of the heat pack and packet combination, after the patch has been sealed to the package about three sides of the patch, leaving one side unsealed, the trigger 40 and crystals 42 are disposed between the first layer 12 and the patch 34. Thereafter, perimetral heat sealing of the patch to the first layer of the heat pack is completed, thereby capturing the trigger and salt crystals within the interior 44 of the packet. Further, in a preferred embodiment, the perimetral seal 46 provided for bonding the perimeter of the patch to the first layer of the heat pack, may be a relatively thin walled polyetheylene seal layer or the perimetral bond may be of lesser sealing strength than the sealing strength of the perimetral seal 16 between the first and second layers of the heat pack itself.

Figure 6:
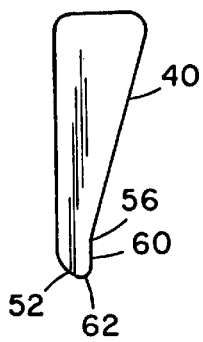
FIG. 6 is an elevational view of one embodiment of a trigger employed in the apparatus of the present invention.
Figure 7:
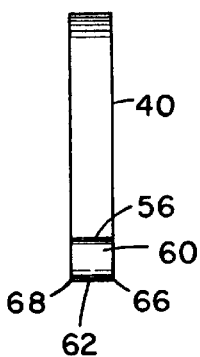
FIG. 7 is a side elevational view of the trigger depicted in FIG. 6.
Figure 8:
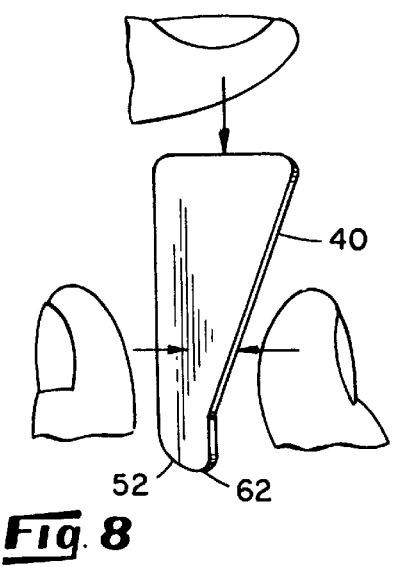
FIG. 8 is a representation depicting one mode of activation of the trigger employed in the present invention.

In accordance with one aspect of the present invention, the trigger 40 is fabricated from a solid plastic comprising an elongated planar body portion 50 and first and second ends 52 and 54, respectively. A suitable plastic for fabrication of the trigger is polyethylene. Preferably the material from which the trigger if fabricated is opaque so that the trigger is readily recognizable within the packet. In the preferred trigger, the first end 52 thereof is provided with a substantially flat surface for engagement therewith of a force-developing instrumentality, such as the finger or thumb of a medical technician. The body portion 50 of the trigger is tapered in width from the first end 52 thereof inwardly to a minimum width location 56 adjacent the second end 54. The opposite and second end 54 of the trigger, in a preferred embodiment, is provided with a multi-radius "hooked" portion 56 which provides a blunt end to the trigger as best seen in FIGS. 6–8. Employing multiple radii to define the blunt second end of the trigger provides protection against inadvertent rupture of the packet, while also providing for the desired ability to deliberately rupture the packet to introduce salt crystals from the packet into the supercooled salt solution contained in the pouch. In a specific example of a suitable trigger, the body portion is about 1 inch long, 1/16 inch thick, and tapers from a maximum width of 3/8 inch at its first end 52 to a minimum width of 1/8 inch adjacent the commencement of the radiusing of the second end 54. At the second end 54, commencing at the minimum width location 56, the hooked portion of the end 54 includes a straight side wall portion 60 which terminates just short of the extreme tip 62 of the end 54. Again commencing at the minimum width location 56, the side wall 58 opposite the straight side wall portion 60 is radiused with a first radius that extends from the location minimum width 56 to the extreme tip 62 of the end 54. The extreme tip of the end 54 is further radiused with a more severe second radius that extends between the first radius and the termination of the side wall portion 60. In the given example, a first radius of 0.1250 inch and a second radius of 0.0250 inch are suitable for providing the desired blunt end 54 for the trigger. Preferably, the thickness of the trigger is substantially uniform so that the blunt end 54 of the trigger includes opposite square side edges 66 and 68. It will be recognized that other radii, and dimensions of the trigger may be employed so long as the blunt end 54 of the trigger can not be made to pierce the wall of either the patch 34 or the layer 12 of the heat pack without inordinate manipulation of the trigger, but the trigger can be caused to pierce the sealed seam 41 of the patch to the heat pack wall in an area adjacent the blunt end of the trigger.

In the present apparatus, it is important that the trigger pierce the packet in which it is contained in only a limited region. In accordance with the present invention, this region is delimited by several factors. First, the packet 30 is formed with an elongated rectangular cavity which is sized and shaped, relative to the dimensions of the trigger, to ensure that once the trigger is properly initially disposed with its packet, and that at all times thereafter, the trigger remains oriented within the packet such that the blunt end 54 of the trigger is oriented adjacent that limited region wherein piercing of the packet is to be accomplished. Further, the blunt end of the trigger is configured such that it will not pierce the material of the patch 34 or the layer 12 of the heat pack under any circumstances other than by very deliberate and inordinate manipulation of the trigger. Still further, in accordance with one aspect of the present invention, the strength of the perimetral seal 46 between the patch 34 and the inner wall 36 of the layer 12 of the heat pack is chosen to be less than the strength of the perimetral seal 16 of the heat pack itself. Thus, the trigger can only pierce the packet at the seal 46, and, because of the ordered orientation of the trigger within the packet, piercing of the seal 46 can only occur in a limited portion of the seal, that limited portion being located adjacent the blunt end of the trigger. Enablement of the blunt end of the trigger is enhanced by reason of the square side edges 66 and 68 on the blunt end of the trigger.

The preferred maneuver for effecting piercing of the packet by the trigger is depicted in FIG. 8 where is it seen that the trigger, while disposed within the flexible packet and heat pack, is to be grasped between the thumb and finger of a medical technician, for example, to provide guidance for movement of the trigger within the packet. Thereupon, the technician engages the first end of the trigger with another finger and applies a force thereto which causes the trigger to slide between the finger and thumb of the technician and for the blunt end of the trigger to engage the perimetral seal 46. Upon the engagement of the trigger with the seal, the square edges of the end of the trigger function to apply lateral pressure against the seal. Further movement of the trigger in the direction of the seal results in full rupture of the seal in the limited region where the end of the trigger is in engagement with the seal. Upon rupture of the seal, the blunt end of the trigger enters the pouch 24 of the heat pack, carrying with such end a quantity of the salt crystals which were initially stored within the packet with the trigger. Only a very few salt crystals are necessary to initiate crystallization of the supercooled salt solution. In accordance with one feature of the present invention, the inventor ensures that the entry of the trigger into the ruptured area of the seal does not seal off the rupture against the entry of salt crystals into the pouch 24. As noted hereinabove, the end of the trigger is provided with a "hooked" portion. This "hooked" portion develops a type of pocket in the region of the junction between the tapered portion of the side wall and the straight portion of this side wall. Salt crystals are captured within this pocket such that the crystals are not scrapped off the trigger as it passes through the rupture in the seal, but rather the crystals are carried into the pouch 24 unimpeded by their passage through the rupture in the seal. Upon their introduction into supercooled salt solution, the crystals initiate crystallization of the salt solution with resulting generation of heat.

What is claimed:

1. In a flexible heat pack package containing a supercooled salt solution, the improvement comprising a flexible packet at least partially contained within the heat pack package and exposed to the salt solution contained therein, a trigger contained within said flexible packet, said trigger including a substantially elongated planar body portion having opposite first and second ends, said first end defining means for piercing said flexible packet, said second end defining a blunt surface for engagement by a force-producing instrumentality, said force being directable generally along a plane of said body portion in a direction toward said first end, and wherein said means for piercing said flexible packet defined by said first end of said trigger is of a geometry which is substantially incapable of piercing said flexible package at a location on said flexible package other than a side seam thereof, a chemical moiety capable of activating crystallization of said supercooled salt solution contained in said heat pack package carried by at least said first end of said trigger, whereby upon the application of said force to said second end of said trigger, said first end is caused to penetrate said flexible packet and enter said heat pack package and introduce said chemical moiety to said supercooled salt solution and effect crystallization of said salt solution with resultant production of heat.

2. The improvement of claim 1 wherein said flexible package includes first and second layers of flexible plastic which are overlaid and sealed to one another about the perimeter of the overlaid layers.

3. The improvement of claim 2 wherein said flexible packet comprises a single patch of flexible plastic which is overlaid onto one of said first and second layers and between said first and second layers and sealed about its perimeter.

4. The improvement of claim 3 wherein the seal about the perimeter of the patch overlaid onto one of said first and second layers is more readily piercable than the seal about the perimeter of said flexible package.

\* \* \* \* \*